US009468545B2

(12) United States Patent
Dunn

(10) Patent No.: US 9,468,545 B2
(45) Date of Patent: Oct. 18, 2016

(54) BIFURCATED GRAFT DEVICE

(71) Applicant: W. L. Gore & Associates, Inc., Newark, DE (US)

(72) Inventor: Annette Dunn, Scottsdale, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 14/667,883

(22) Filed: Mar. 25, 2015

(65) Prior Publication Data

US 2015/0282959 A1    Oct. 8, 2015

Related U.S. Application Data

(60) Provisional application No. 61/975,688, filed on Apr. 4, 2014.

(51) Int. Cl.
*A61F 2/06*    (2013.01)
*A61F 2/856*    (2013.01)
*A61F 2/07*    (2013.01)

(52) U.S. Cl.
CPC .............. *A61F 2/856* (2013.01); *A61F 2/07* (2013.01); *A61F 2002/065* (2013.01); *A61F 2002/072* (2013.01); *A61F 2230/0065* (2013.01); *A61F 2230/0067* (2013.01); *A61F 2230/0095* (2013.01); *A61F 2240/001* (2013.01); *A61F 2240/002* (2013.01); *Y10T 156/10* (2015.01)

(58) Field of Classification Search
CPC .......... A61F 2/856; A61F 2/07; A61F 2/852; A61F 2002/065; A61F 2002/072; A61F 2230/0065; A61F 2230/0067
USPC ............................... 623/1.35, 1.13
See application file for complete search history.

(56) References Cited

U.S. PATENT DOCUMENTS

| 2,952,149 | A | | 9/1960 | Halliday et al. | |
|---|---|---|---|---|---|
| 5,632,772 | A | * | 5/1997 | Alcime | A61F 2/07 623/1.35 |
| 5,755,735 | A | | 5/1998 | Richter et al. | |
| 6,017,363 | A | * | 1/2000 | Hojeibane | A61F 2/856 606/194 |
| 6,099,560 | A | * | 8/2000 | Penn | A61F 2/91 623/1.35 |
| 6,102,940 | A | * | 8/2000 | Robichon | A61F 2/07 623/1.35 |
| 6,183,509 | B1 | * | 2/2001 | Dibie | A61F 2/91 623/1.16 |

(Continued)

FOREIGN PATENT DOCUMENTS

| DE | 10 2006 058908 | 4/2008 |
|---|---|---|
| WO | 2010/027677 | 3/2010 |

OTHER PUBLICATIONS

International Search Report and Written Opinion for PCT/US2015/022684 mailed Jun. 10, 2015, corresponding to U.S. Appl. No. 14/667,883, 5 pages.

*Primary Examiner* — Alvin Stewart

(57) ABSTRACT

A bifurcated graft including a first branch having a first leg graft; a second branch having a second leg graft spaced apart from and not overlapping the first leg graft; and a trunk including a first layer having a first portion, a second portion, and a saddle extending therebetween the first portion and the second portion. Each of the first portion and second portion have opposite side edges that are spaced apart to define a first width. The saddle has opposite sides that are spaced apart to define a second width. The second width of the saddle is less than the first width of each of the first portion and second portion. The saddle extends along a bifurcation between the first leg graft and second leg graft.

20 Claims, 5 Drawing Sheets

(56) References Cited

U.S. PATENT DOCUMENTS

| | | | |
|---|---|---|---|
| 6,203,568 B1 * | 3/2001 | Lombardi | A61F 2/07 600/36 |
| 6,210,433 B1 * | 4/2001 | Larre | A61F 2/86 623/1.15 |
| 6,428,567 B2 * | 8/2002 | Wilson | A61F 2/856 623/1.11 |
| 6,451,053 B1 | 9/2002 | Dehdashtian et al. | |
| 6,454,796 B1 * | 9/2002 | Barkman | A61F 2/07 623/1.35 |
| 6,508,835 B1 * | 1/2003 | Shaolian | A61F 2/90 623/1.13 |
| 6,514,281 B1 * | 2/2003 | Blaeser | A61F 2/954 623/1.12 |
| 6,610,087 B1 * | 8/2003 | Zarbatany | A61F 2/86 606/194 |
| 6,666,884 B1 * | 12/2003 | Webster | A61F 2/86 623/1.1 |
| 6,685,738 B2 * | 2/2004 | Chouinard | A61F 2/90 606/200 |
| 6,811,566 B1 | 11/2004 | Penn et al. | |
| 6,827,731 B2 | 12/2004 | Armstrong et al. | |
| 8,257,431 B2 | 9/2012 | Henderson et al. | |
| 2004/0138736 A1 | 7/2004 | Obara | |
| 2005/0234542 A1 * | 10/2005 | Melsheimer | A61F 2/07 623/1.35 |
| 2006/0041091 A1 | 2/2006 | Chang et al. | |
| 2006/0178733 A1 * | 8/2006 | Pinchuk | A61F 2/07 623/1.35 |
| 2008/0103587 A1 | 5/2008 | Henderson et al. | |
| 2010/0137969 A1 * | 6/2010 | Rakos | A61F 2/06 623/1.13 |
| 2011/0208289 A1 | 8/2011 | Shalev | |
| 2015/0081007 A1 * | 3/2015 | Joye | A61F 2/856 623/1.11 |
| 2015/0282959 A1 * | 10/2015 | Dunn | A61F 2/856 623/1.35 |

* cited by examiner

BIFURCATED GRAFT DEVICE

FIELD

The present disclosure relates to endoluminal stent graft devices. More particularly, the present disclosure relates to construction of stent graft devices.

BACKGROUND

Bifurcated stent graft devices are known in the art for treating abdominal aortic aneurysms. Such devices can be delivered endoluminally. It remains desirable to provide bifurcated stent graft devices that allow low profile delivery at 12 fr or less.

BRIEF DESCRIPTION OF THE DRAWINGS

The accompanying drawings are included to provide a further understanding of the present disclosure and are incorporated in and constitute a part of this specification, illustrate embodiments of the present disclosure, and together with the description serve to explain the principles of the present disclosure.

DETAILED DESCRIPTION

Figure 1:
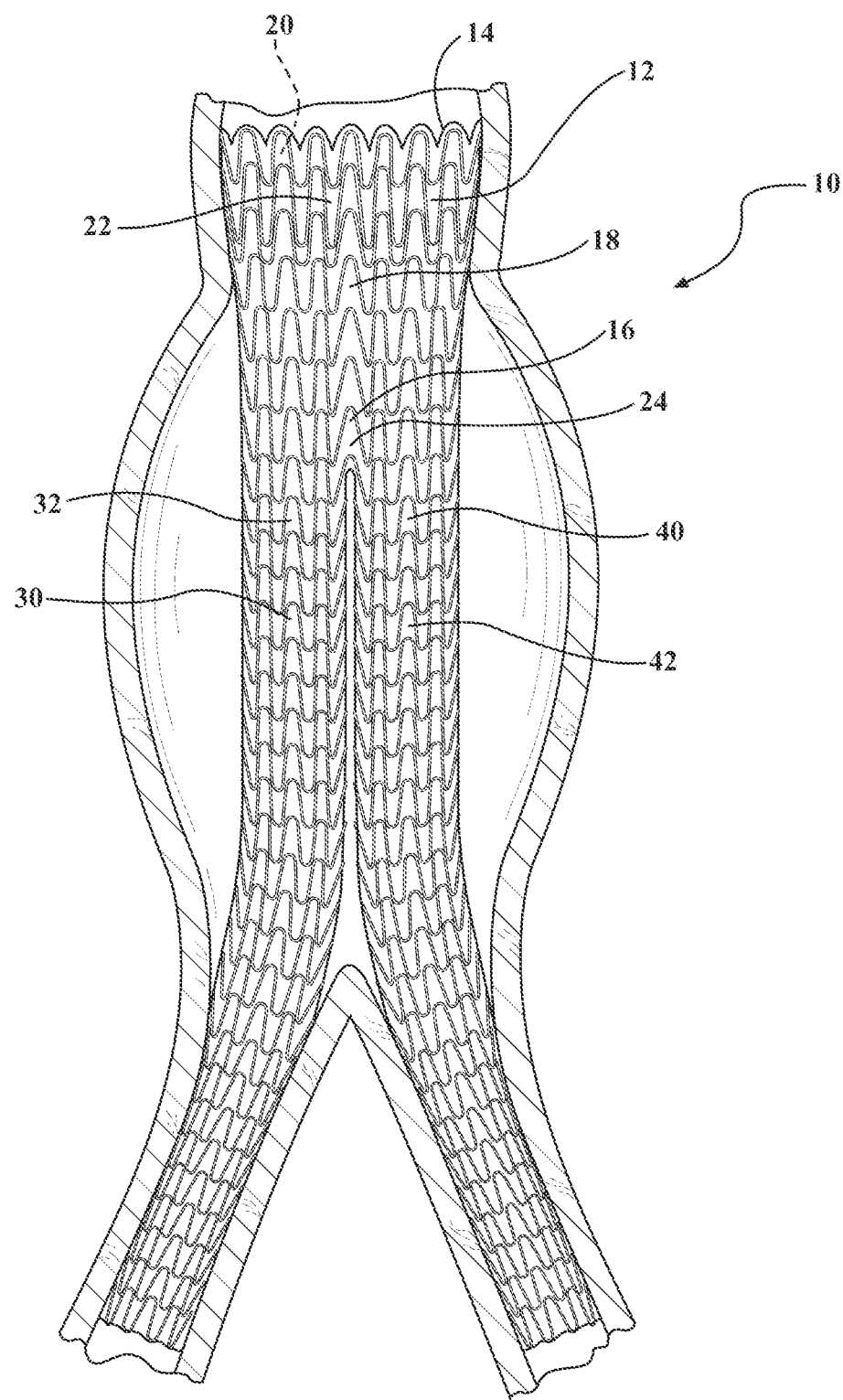
FIG. 1 is a front elevational view of a bifurcated graft device.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

Throughout this specification and in the claims, the term "distal" refers to a location that is, or a portion of an endoluminal device (such as a stent-graft) that when implanted is, further downstream with respect to blood flow than another portion of the device. Similarly, the term "distally" refers to the direction of blood flow or further downstream in the direction of blood flow.

The term "proximal" refers to a location that is, or a portion of an endoluminal device that when implanted is, further upstream with respect to blood flow than another portion of the device. Similarly, the term "proximally" refers to the direction opposite to the direction of blood flow or upstream from the direction of blood flow.

With further regard to the terms proximal and distal, and because the present disclosure is not limited to peripheral and/or central approaches, this disclosure should not be narrowly construed with respect to these terms. Rather, the devices and methods described herein can be altered and/or adjusted relative to the anatomy of a patient.

Throughout this specification and in the claims, the term "leading" refers to a relative location on a device which is closer to the end of the device that is inserted into and progressed through the vasculature of a patient. The term "trailing" refers to a relative location on a device which is closer to the end of the device that is located outside of the vasculature of a patient.

As the term "thermoplastic" is used herein it defines a polymer that softens when exposed to heat and returns to its original condition when cooled to room temperature. Such a polymer can be made to soften, flow or take on new shapes, without significant degradation or alteration of the polymer's original condition, by the application of heat or heat and pressure.

In contrast to a thermoplastic polymer, a "thermoset" polymer is hereby defined as a polymer that solidifies or "sets" irreversibly when cured. A determination of whether a polymer is a "thermoplastic" polymer within the meaning of the present invention can be made by slowly elevating the temperature of a stressed specimen and watching for deformation. If the polymer can be made to soften, flow, or take on a new shape, without significant degradation or alteration of the polymer's original chemical condition, then the polymer is considered to be a thermoplastic.

Referring to FIG. 1, a bifurcated graft device 10 includes a generally tubular or cylindrical trunk 12 having a proximal end 14 and an opposite distal end 16. The trunk 12 includes an outer surface 18 and an opposite inner surface 20 defining a main lumen 22 that extends longitudinally between the proximal 14 and distal 16 ends of the trunk 12. The distal end 16 of the trunk is generally frustoconically-shaped. The graft device 10 includes a tubular or cylindrical first leg 30 extending from the distal end 16 of the trunk 12 and defining a first branch lumen 32. The graft device 10 also includes a tubular or cylindrical second leg 40 extending from the distal end 16 of the trunk 12 and defining a second branch lumen 42. The first branch lumen 32 and second branch lumen 42 intersect at a bifurcation region 24 and are in fluid communication with the main lumen 22.

Figure 2:
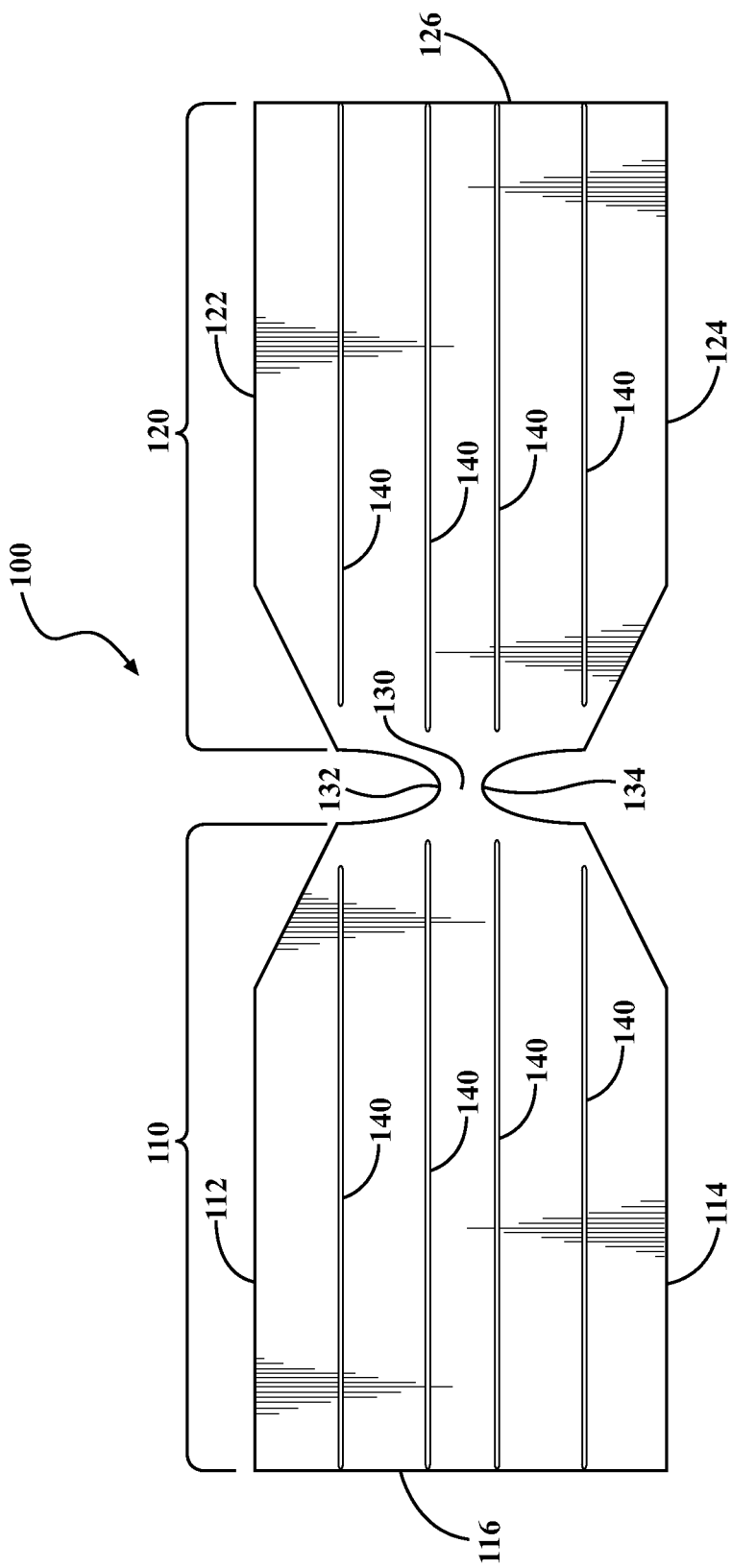
FIG. 2 is a plan view of a layer used in the construction of the bifurcated graft device in accordance with various embodiments.

In various embodiments, for example as shown in FIG. 2, the trunk 12 comprises a first layer 100 of biocompatible material. The first layer 100 can be fabricated by various methods known in the art. These methods include, but are not limited to extrusions, molding, spray coating, dip coatings and film paving. The first layer 100 can comprise a single material or multiple materials. The materials can be selected to produce the desired strength, thickness, permeability, flexibility or other properties. The first layer 100 can be a laminated series of film layers comprised of the same or different materials. The laminated film layers can be adhered together by a thermo-compression process using thermo-set or thermo-plastic adhesives.

Suitable materials for the laminated film layers and adhesives can include polymers such as nylon, polyacrylamide, polycarbonate, polyformaldehyde, polymethylmethacrylate, polytetrafluoroethylene, polytrifluorochlorethylene, polyvinylchloride, polyurethane, elastomeric organosilicon polymers, polyethylene, polypropylene, polyurethane, polyglycolic acid, polyesters, polyamides, their mixtures, blends and copolymers. Other suitable materials can be of a class of polyesters such as polyethylene terephthalate including DACRON® and MYLAR® and polyaramids such as KEVLAR®, polyfluorocarbons such as polytetrafluoroethylene (PTFE) with and without copolymerized hexafluoropropylene (TEFLON® or GORE-TEX®), and porous or nonporous polyurethanes.

In another embodiment, the first layer can comprise expanded fluorocarbon polymer materials, including PTFE, described in British. Pat. Nos. 1,355,373; or 1,506,432 or in U.S. Pat. Nos. 3,953,566; 4,187,390. Included in the class of fluoropolymers are polytetrafluoroethylene (PTFE), fluorinated ethylene propylene (FEP), copolymers of tetrafluoroethylene (TFE) and perfluoro (propyl vinyl ether) (PFA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinyfluoride (PVF).

Additional suitable materials include, but are not limited to, vinylidinefluoride/hexafluoropropylene hexafluoropropylene (HFP), tetrafluoroethylene (TFE), vinylidenefluoride, 1-hydropentafluoropropylene, perfluoro (methylvinyl ether), chlorotrifluoroethylene (CTFE), pentafluoropropene, trifluoroethylene, hexafluoroacetone, hexafluoroisobutylene, fluorinated poly(ethylene-co-propylene) (FPEP), poly(hexafluoropropene) (PHFP), poly(chlorotrifluoroethylene) (PCTFE), poly(vinylidene fluoride (PVDF), poly(vinylidene fluoride-co-tetrafluoroethylene) (PVDFTFE), poly(vinylidene fluoride-co-hexafluoropropene) (PVDF-HFP), poly(tetrafluoroethylene-co-hexafluoropropene) (PTFE-HFP), poly(tetrafluoroethylene-co-vinyl alcohol) (PTFE-VAL), poly(tetrafluoroethylene-co-vinyl acetate) (PTFE-VAC), poly(tetrafluoroethylene-co-propene) (PTFEP) poly(hexafluoropropene-co-vinyl alcohol) (PHFPVAL), poly(ethylene-co-tetrafluoroethylene) (PETFE), poly (ethylene-co-hexafluoropropene) (PEHFP), poly(vinylidene fluoride-co-chlorotrifluoroe-thylene) (PVDF-CTFE), and combinations thereof, and additional polymers and copolymers described in U.S. Publication 2004/0063805.

Additional polyfluorocopolymers include tetrafluoroethylene (TFE)/perfluoroalkylvinylether (PAVE). PAVE can be perfluoromethylvinylether (PMVE), perfluoroethylvinylether (PEVE), or perfluoropropylvinylether (PPVE), as essentially described in U.S. Publication 2006/0198866 and U.S. Pat. No. 7,049,380. Other polymers and copolymers include, polylactide, polycaprolacton-glycolide, polyorthoesters, polyanhydlides; poly-aminoacids; polysaccharides; polyphosphazenes; poly(ether-ester) copolymers, e.g., PEO-PLLA, or blends thereof, polydimethyl-siolxane; poly(ethylene-vingylacetate); acrylate based polymers or copolymers, e.g., poly(hydroxyethyl methylmethacrylate, polyvinyl pyrrolidinone; fluorinated polymers such as polytetrafluoroethylene; cellulose esters and any polymer and copolymers described in U.S. Publication 2004/0063805.

The individual film layers can be supplied with an adhesive pre applied to one or both film surfaces. For example, any suitable adhesive can be coated, sprayed or otherwise applied to a film. An example of a suitable pre-applied adhesive is thermo-plastic FEP. The thermo-plastic adhesive can then be used to bond individual film layers together, forming a laminated structure.

The laminated film layers can have directional properties such as a high tensile strength along a first axis and a low tensile strength along a second axis. These directional strengths can be used to dictate a particular overall strength of a film laminate structure. For an example, several layers of films can be layered with the high strength directionality along a single axis. The films could also be applied with the high strength directionality of individual film layers orientated at for example, 90° from each other, resulting in a laminate with a balanced strength along two different axis.

The angular orientation between the film layers can be selected to produce a desired strength orientation of the final laminate.

The film laminate thickness can be dictated by the number of film layers applied and by the thickness of the individual films. For example, the laminate thickness can range from about 0.01 mm to about 10 mm. Individual film thicknesses can range from about 0.001 mm to about 1 mm. Graft constructs in accordance with various embodiments are described in detail below which will allow use of thin polymer films toward the thinner end of the above thickness range to create low-profile graft devices that allow delivery of such devices at a 12 fr or less delivery profile.

Still referring to FIG. 2, the first layer 100 includes a first portion 110, a second portion 120 spaced apart from the first portion 110, and a saddle 130 extending between and interconnecting the first portion 110 and second portion 120. The first portion 110 extends over a generally rectangular shaped area having a width generally defined between spaced apart side edges 112, 114, and a height generally defined between a transversely extending terminal edge 116 that extends between the side edges 112, 114 and the saddle 130. Similarly, the second portion 120 extends over a generally rectangular shaped area having a width generally defined between spaced apart side edges 122, 124, and a height generally defined between a transversely extending terminal edge 126 that extends between the side edges 122, 124 and the saddle 130. In a number of embodiments, the combined width of the first portion 110 and second portion 120 of the trunk 12 approximates the circumference of the trunk 12. The transversely extending terminal edges 116, 126 of the first portion 110 and the second portion 120 together define the general periphery of the proximal end 14 of the trunk 12. The saddle 130 has a width defined between generally mirror-opposite and spaced apart sides 132, 134. The width of the saddle 130 between the sides 132, 134 is substantially reduced relative to the width of each of the first portion 110 and the second portion 120. Each of the first 110 and second 120 portions can taper in width toward the saddle 130.

In various embodiments, the first layer 100 can be a laminate of several film layers comprised of several different types of films and thermo-plastic adhesives. The films can be layered onto a flat substrate, onto a cylindrical mandrel or any desired shaped substrate. The layered films can then be bonded together by heating and reflowing the thermo-plastic adhesive to form the first layer.

The first layer can be constructed from a single layer of a first film having a high tensile strength directionality along a single axis, as indicated at directional lines 140 in FIG. 2. A single layer of a second film of thin FEP can then be positioned onto the first film. A single layer of a third film can then be positioned onto the second film. The third film can have a low tensile strength directionality (oriented approximately 90° from the first layer high strength axis). The third film can be supplied with a thin pre-applied layer of FEP. The third film can be positioned onto the second film with the pre-applied FEP facing away from the second film. A single layer of a fourth film can then be positioned onto the third film. The fourth film can have a low tensile strength directionality (oriented approximately 90° from the third layer low strength axis). The fourth film can be supplied with a thin pre-applied layer of FEP. The fourth film can be positioned onto the third film with the pre-applied FEP facing away from the third film. The outermost fourth film layer therefore has a thin pre-applied layer of FEP facing outward to permit attachment to other films, partially constructed devices, support frames or any other desired component.

Figure 3:
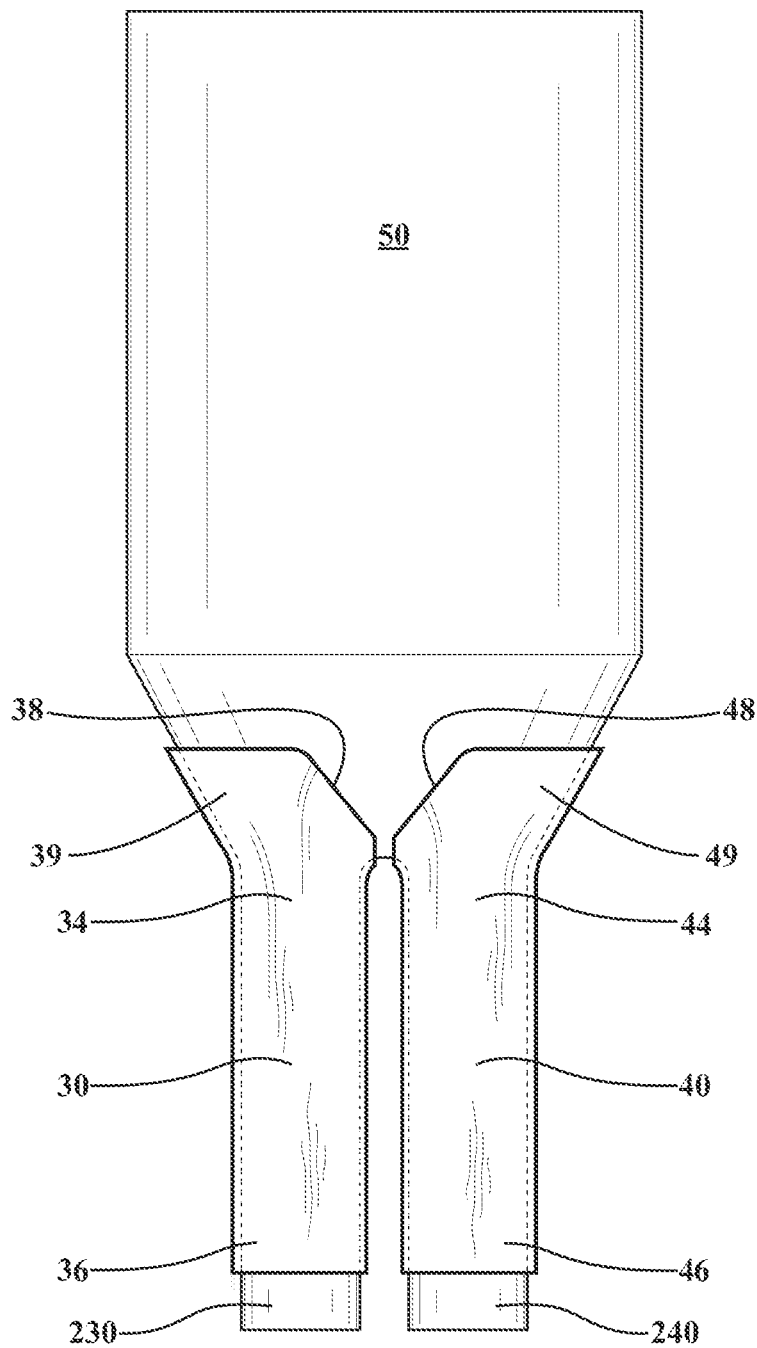
FIGS. 3-5 illustrate construction of a bifurcated graft device in accordance with various embodiments.
Figure 4:
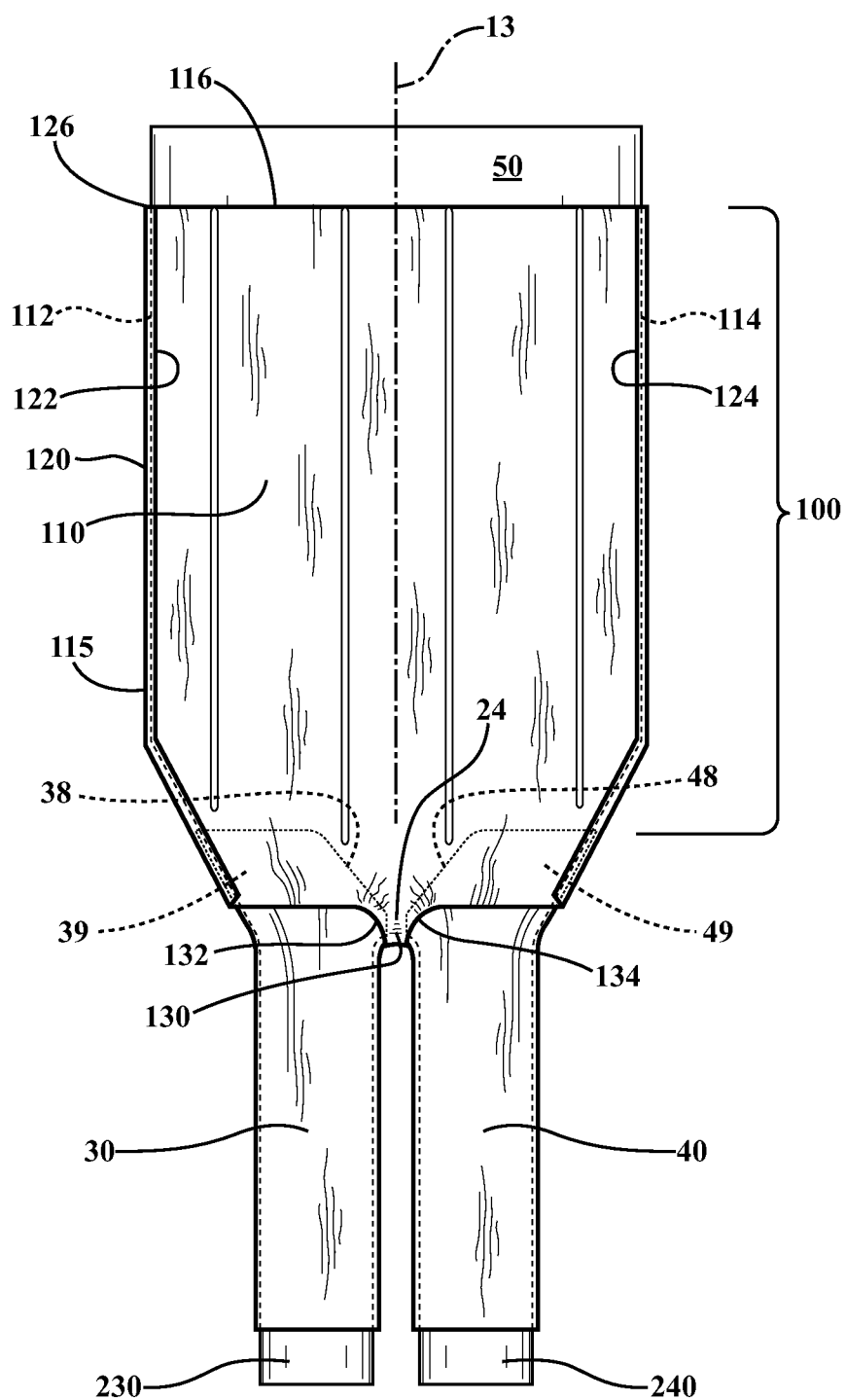
Figure 5:
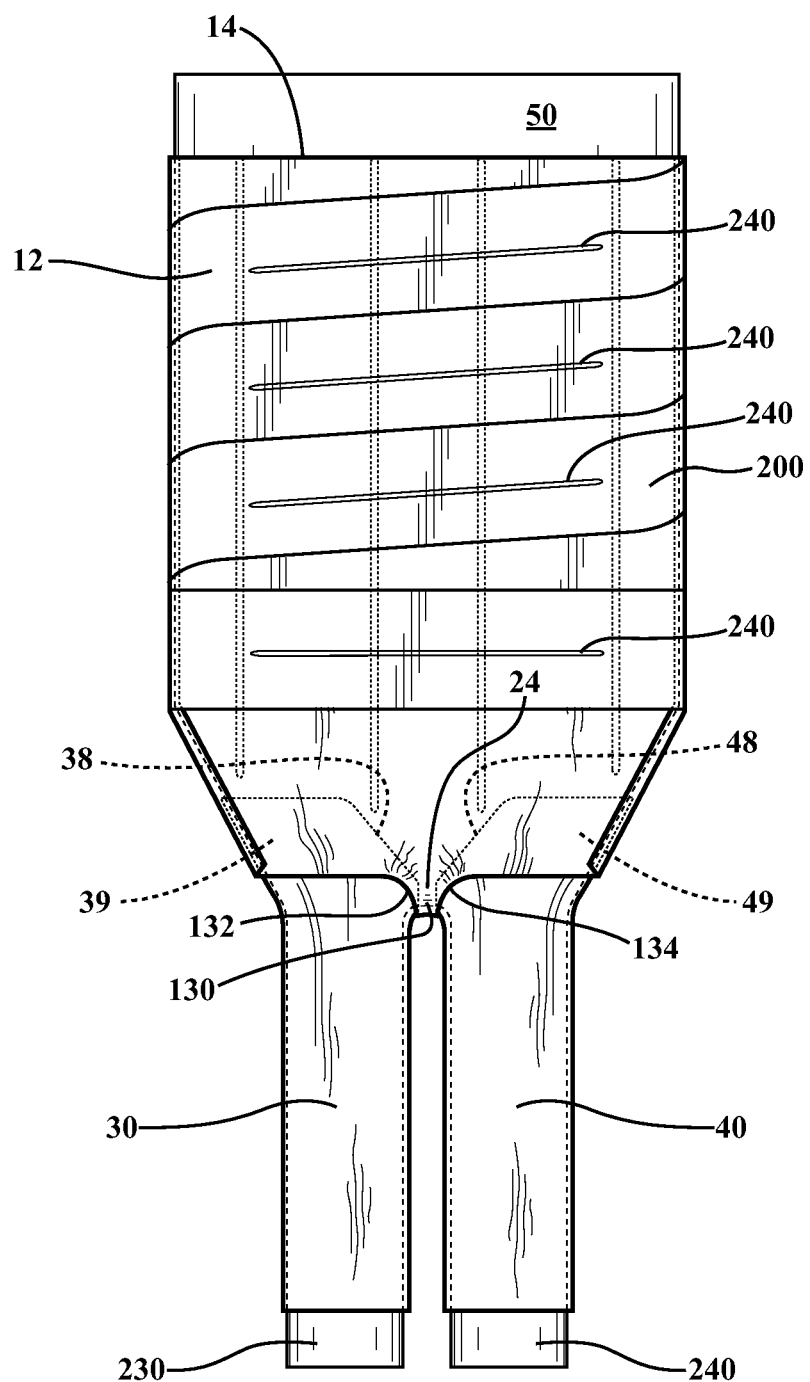

In various embodiments, the first layer can be incorporated into the trunk structure such that the high tensile strength direction is generally aligned with the longitudinal axis of the trunk. For example, as illustrated in FIGS. 3-5, a mandrel 50 can be utilized in the constructions of the graft device. The mandrel 50 has a shape approximating the bifurcated configuration of the graft device 10. More specifically, the mandrel 50 includes a trunk section and leg sections 230, 240 extending from an end of the trunk section. Separate first 30 and second 40 legs are constructed and inserted over respective leg sections 230, 240 of the mandrel, as shown in FIG. 3. Each leg 30, 40 includes a proximal end 34, 44 and an opposite distal end 36, 46. Each leg 30, 40 includes a tail 39, 49 extending from the proximal ends 34, 44. Sides 38, 48 of the tails 39, 49 are circumferentially spaced apart from each other to define windows on opposite sides of the mandrel 50. The tails 39, 49 and the first layer 100 overlap each other. Overlap between the legs 30, 40 and the first layer 100 is, however, minimized or otherwise avoided at the bifurcation region 24 to facilitate low profile when the device 10 is compacted for endoluminal delivery.

Referring to FIG. 4, the first layer 100 is applied onto the mandrel 50. The tails 39, 49 of the legs 30, 40 and the first layer 100 overlap each other. The saddle 130 is centered over and extends along the bifurcation region 24. The sides 132, 134 of the saddle 130 can also drape or overlap with the legs 30, 40 on either side of the bifurcation region 24. The high tensile strength direction 140 is generally aligned with the longitudinal axis 13 of the trunk 12. The side edges 112, 122 and 114, 124 are aligned with each other along the mandrel 50. Optionally, the side edges 112, 122 and 114, 124 can be overlapped. The transversely extending terminal edges 116, 126 are aligned to define the periphery of the proximal end 14 of the trunk 12.

Referring to FIG. 5, a second layer 200 is wrapped helically about the trunk region of the mandrel 50 over the first layer 100. The second layer 200 can be constructed from a laminate of several film layers comprised of several different types of films and thermo-plastic adhesives, as earlier discussed. The films can be layered onto a flat substrate, onto a cylindrical mandrel or any desired shaped substrate. The layered films can then be bonded together by heating and reflowing the thermo-plastic adhesive to form the second layer.

In various embodiments, the second layer 200 can be incorporated into the trunk structure such that the high tensile strength direction of the wrap, as indicated at 240 in FIG. 5, is generally aligned with the helical wrap direction.

The graft device construct in FIG. 5 can be heated to a sufficient temperature to soften and reflow the thermoplastic adhesives such that the first layer 100, second layer 200 and tails 39, 49 of the legs 30, 40 are bonded together. The resulting graft structure can then be removed from the mandrel 50 and bonded to a stent structure to form the bifurcated graft device 10.

It will be apparent to those skilled in the art that various modifications and variations can be made in the present disclosure without departing from the spirit or scope of the present disclosure. Thus, it is intended that the present disclosure cover the modifications and variations of this present disclosure provided they come within the scope of the appended claims and their equivalents.

What is claimed is:

1. A bifurcated graft, comprising:
   a first branch having a tubular first leg graft defining a first leg lumen;
   a second branch having a tubular second leg graft defining a second leg lumen, the second leg graft being spaced apart from and not overlapping the first leg graft; and
   a trunk defining a main lumen, the trunk including a first layer having a first portion, a second portion, and a saddle extending therebetween the first portion and the second portion, each of the first portion and second portion having opposite side edges that are spaced apart to define a first width, the saddle having opposite sides that are spaced apart to define a second width,
   wherein the saddle extends along a bifurcation between the first leg graft and second leg graft, and the second width of the saddle is less than the first width of each of the first portion and second portion.

2. The bifurcated graft of claim 1, wherein each first leg graft and second leg graft includes opposite proximal and distal ends, and a tail extending from the proximal end that at least partially overlaps with both the first portion and second portion of the first layer.

3. The bifurcated graft of claim 2, wherein the trunk includes a substantially cylindrical portion, and a frustoconically shaped portion that extends between the cylindrical portion and the first and second branches.

4. The bifurcated graft of claim 3, wherein the tails of the first and second leg grafts respectively the first and second portions of the first layer along the frustoconically shaped portion of the trunk.

5. The bifurcated graft of claim 3, wherein the sides edges of each of the first and second portions of the trunk are generally parallel with a longitudinal axis of the trunk.

6. The bifurcated graft of claim 5, wherein each side of the first portion overlaps a respective one of the sides of the second portion.

7. A method of manufacturing the bifurcated graft of claim 2, said method comprising:
   providing a mandrel having a trunk section and first and second legs extending from an end of the trunk section;
   placing the first leg graft over the first leg of the mandrel;
   placing the second leg graft over the second leg of the mandrel;
   placing first layer over the trunk section such that the saddle extends along the birfurcation, and the first and second portions extend along opposite sides of the trunk section of the mandrel;
   securing the first and second portions of the first layer to each other along overlapping side edges to form a main lumen; and
   securing the tails of the first and second legs to the overlapping first and second portions of the first layer so that the main lumen is in fluid communication with the first and second leg lumens.

8. The method as set forth in claim 7, wherein the mandrel includes a substantially cylindrical section, and a frustoconically shaped section that extends between the cylindrical section and the first and second legs.

9. The method as set forth in claim 8 including helically wrapping a second layer over the first layer along only the cylindrical section of the mandrel.

10. The method as set forth in claim 9 including heating the mandrel to a sufficient temperature to bond the first layer, second layer and overlapped tails of the legs and removing the resulting bifurcated graft from the mandrel.

11. The method as set forth in claim 10 including bonding the resulting bifurcated graft to a stent structure.

12. The bifurcated graft of claim 1, wherein the opposite sides of the saddle overlap respective first and second leg grafts.

13. The bifurcated graft of claim 1, wherein the trunk includes a proximal end and an opposite distal end, the first and second branches extending from the distal end of the trunk.

14. The bifurcated graft of claim 13, wherein proximal end of the trunk is substantially cylindrically shaped and the distal end is substantially frustoconically shaped.

15. The bifurcated graft of claim 14, wherein each of the first and second portions includes a terminal edge that extends along the proximal end of the trunk, the terminal edges of the first and second portions together approximating a circumference of the proximal end of the trunk.

16. The bifurcated graft of claim 1 including a second layer overlapping the first layer.

17. The bifurcated graft of claim 16, wherein the second layer extends substantially helically about the trunk.

18. The bifurcated graft of claim 17, wherein the trunk includes a substantially cylindrical portion and a frustoconically shaped portion that extends between the cylindrical portion and the first and second branches, the second layer extending only along the cylindrical portion.

19. The bifurcated graft of claim 18, wherein each first leg graft and second leg graft includes opposite proximal and distal ends, and a tail extending from the distal end that at least partially overlaps with both the first portion and second portion of the first layer.

20. The bifurcated graft of claim 19, wherein the overlap between the tails of the first and second leg grafts and the first and second portions of the first layer extends along the frustoconically shaped portion.

* * * * *